United States Patent [19]

Hrebeniuk

[11] Patent Number: Plant 7,338

[45] Date of Patent: Sep. 25, 1990

[54] DISTINCT VARIETY OF POINSETTIA NAMED H-477/86 RED

[76] Inventor: Alexander Hrebeniuk, R.D. -190 1, Box 118, Sugar Run, Pa. 18846

[21] Appl. No.: 338,951

[22] Filed: Apr. 17, 1989

[51] Int. Cl.[5] ..... A01H 5/00

[52] U.S. Cl. ..... Plt./86

[58] Field of Search ..... Plt./86

*Primary Examiner*—Howard J. Locker

*Attorney, Agent, or Firm*—Webb, Burden, Ziesenheim & Webb

[57] ABSTRACT

A Poinsettia plant named H-477/86 Red particularly characterized by the combined characteristics of its dark green leaves, bright red bracts, triple form, prolific bract development, large bloom size, and good shipping characteristics.

1 Drawing Sheet

BACKGROUND OF THE NEW PLANT

The present invention comprises a new and distinct cultivar of *Euphorbia pulcherrima* known by the varietal name H-477/86 Red. The new cultivar was developed in a breeding program and is a seedling resulting from the cross of a male parent C-1 (Ecke variety) and the female parent Dynasty U.S. Plant Pat. No. 6,150.

The new cultivar was discovered in July of 1984 in Sugar Run, Pa.; was first asexually reproduced by cuttings shortly thereafter in Sugar Run, Pa., and has been repeatedly asexually reproduced by cuttings at Sugar Run, Pa. Continued observations from the vegetative cuttings have confirmed that the distinguishing features of this new cultivar come true, remain stable and are retained through successive propagations.

The new cultivar flowers earlier when grown under black cloth as compared to Dynasty. The new cultivar has flat flowers with open centers whereas Dynasty has tight flowers. The grandparent varieties HL-1 (U.S. Plant Pat. No. 4,434) and V-14 (U.S. Plant Pat. No. 4,384) both have drooping flowers with tight centers but fluffy petals. This new cultivar has better resistance to fading and longer keeping time than Dynasty or the grandparent varieties. The new variety also has a fuller plant and heavier stems to hold up the flower as compared to Dynasty and the grandparent varieties.

The following traits are determined to be basic characteristics of this new cultivar which in combination distinguish this Poinsettia as new and distinct:

1. Eight and one-half week response time under black cloth.
2. Five to six large breaks after pinch.
3. May be grown single stem or pinch.
4. Top leaves dark yellow-green.
5. Mature leaves dark yellow-green.
6. Petioles very dark red-purple.
7. Veins in leaves on top dark green, shine on bottom of new leaves; veins are red and on mature leaves the veins are light green.
8. Stem on bottom and top dark green-red.
9. Bracts are bright red.
10. The center of the bloom is very long lasting.
11. The blooms have three layers of bracts, type, flat and fluffy.
12. 28 to 30 bracts have been counted on a fully developed pinch plant bloom.

13. The largest bloom size measured on a single stem pinch plant has been 16 inches in diameter.
14. Bracts range in size on a pinch plant from 3 cm. wide and 7 cm. long, to 8 cm. wide and 17 cm. long.
15. In normal blooming the new cultivars show color in the middle of October and are in full bloom in December; saleable in the beginning of December.
16. Plants ship well.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on eight and one-half week plants. The color readings were determined under natural daylight at Sugar Run, Pa. Color references are primarily to the R.H.S. Colour Chart of The Royal Horticultural Society of London.

The plant:

*Form.*—Triple.

*Growth habit.*—Very compact, medium height and freely branching.

*Rooting.*—Very fast and even.

*Blooming season.*—Eight and one-half weeks.

*Blooming habit.*—Large bracts, flat-fluffy develop in treble rows with excellent quality.

Foliage:

*Size.*—From 7 cm. wide and 10 cm. long to 11 cm. wide and 16 cm. long.

*Quantity.*—Up to 15 leaves per flowering stem.

*Color.*—New Foliage — Upper side, Yellow Green Group 147 A. Under side, Yellow Green Group 147 B. Old foliage — Upper side, Yellow Green Group 147 A. Under side, Yellow Green Group 147 B. Leaf petiole — Red-Purple Group 59 A on pinched plant.

*Shape.*—Oak and heart shaped on pinched plant.

*Texture.*—Upper side is smooth and waxy; under side is rough because of veins.

*Edge of margin.*—varied degrees of waviness with leaf tips varying from acuminate to cuspidate.

*Disease resistance.*—resistant to Botrytis.

Flower:

*Borne.*—In a compound corymb.

*Quantity.*—18 to 20 per stem; each flower having a nectary.

*Color.*—Generally Green Group 139 C, Orange Group 28 A, and Red Group 53 A.

Bracts:

*Size.*—3 cm. wide and 7 cm. long to 8 cm. wide and 17 cm. long.

*Quantity.*—28 to 30 bracts on a fully developed pinched plant, which is approximately 16 inches in diameter.

*Color.*—Upper side, Red Group 45 A. Under side, Red Group 45 B.

Reproductive organs: Typical for poinsettia cultivars.

I claim:

1. A new and distinct variety of Poinsettia plant as herein shown and described, particularly characterized by its dark green leaves, bright red bracts, triple form, prolific bract development, large bloom side, and good shipping characteristics.

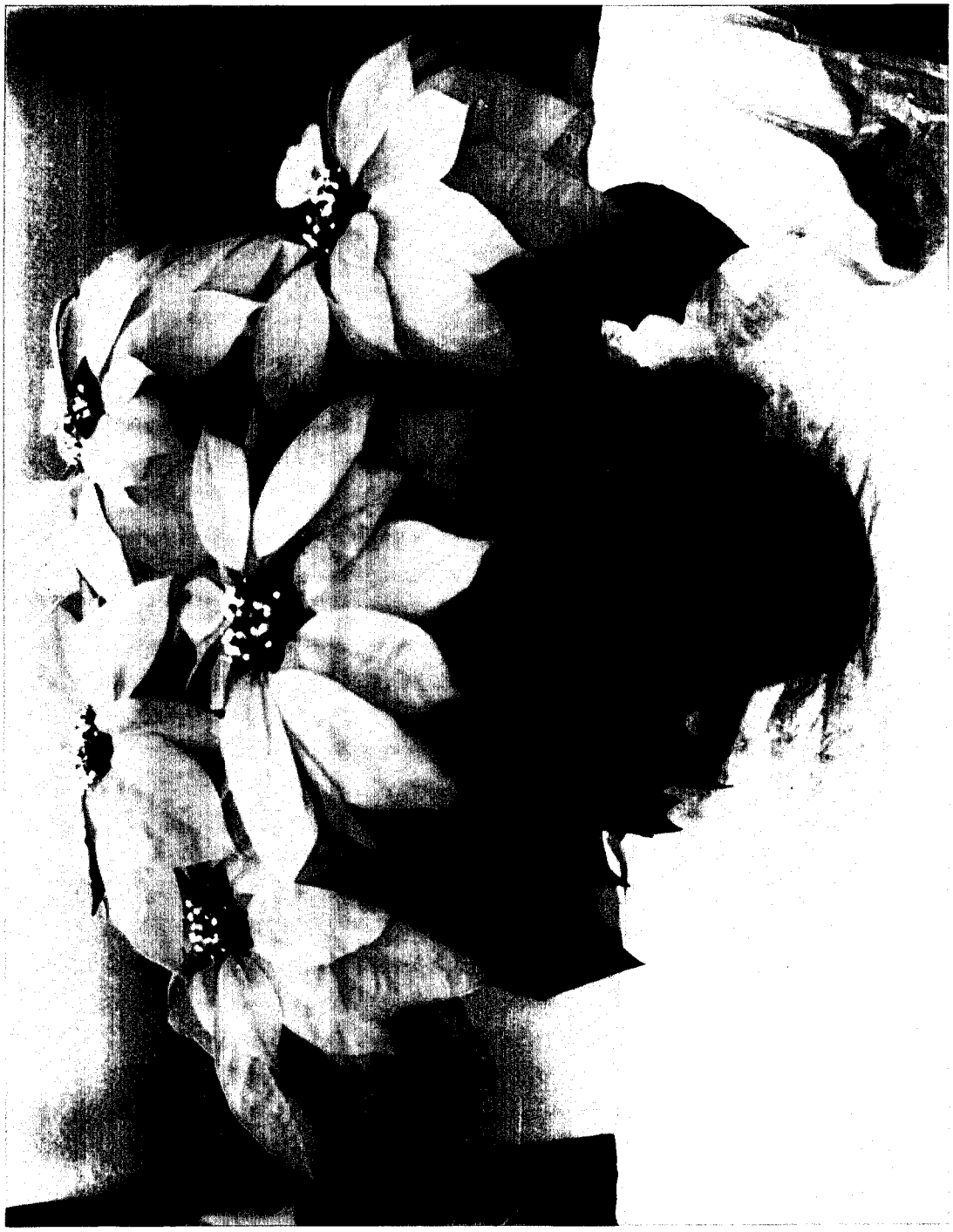

* * * * *